United States Patent
Kimura et al.

(10) Patent No.: US 11,286,219 B2
(45) Date of Patent: Mar. 29, 2022

(54) METHOD FOR PRODUCING INDENE

(71) Applicant: ENEOS CORPORATION, Tokyo (JP)

(72) Inventors: Nobuhiro Kimura, Tokyo (JP); Atsushi Segawa, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 0 days.

(21) Appl. No.: 17/041,193

(22) PCT Filed: Apr. 12, 2019

(86) PCT No.: PCT/JP2019/016050
§ 371 (c)(1),
(2) Date: Sep. 24, 2020

(87) PCT Pub. No.: WO2019/208281
PCT Pub. Date: Oct. 31, 2019

(65) Prior Publication Data
US 2021/0024440 A1  Jan. 28, 2021

(30) Foreign Application Priority Data
Apr. 27, 2018  (JP) .............................. JP2018-087332

(51) Int. Cl.
| | | |
|---|---|---|
| *C07C 5/333* | (2006.01) | |
| *B01J 21/00* | (2006.01) | |
| *B01J 21/10* | (2006.01) | |
| *B01J 23/62* | (2006.01) | |

(52) U.S. Cl.
CPC ........... *C07C 5/3337* (2013.01); *B01J 21/005* (2013.01); *B01J 21/10* (2013.01); *B01J 23/626* (2013.01); *C07C 2521/04* (2013.01); *C07C 2521/10* (2013.01); *C07C 2523/62* (2013.01)

(58) Field of Classification Search
CPC .............. C07C 5/3337; C07C 2521/04; C07C 2521/10; C07C 2523/14; C07C 2523/42; C07C 2523/62; C07C 2602/08; B01J 21/005; B01J 21/10; B01J 23/42; B01J 23/626
See application file for complete search history.

(56) References Cited

U.S. PATENT DOCUMENTS

| | | | |
|---|---|---|---|
| 4,143,082 A | 3/1979 | Bartek et al. | |
| 4,291,181 A * | 9/1981 | Kiikka | ................. C07C 5/3332 585/320 |
| 4,430,517 A * | 2/1984 | Imai | ........................ B01J 23/56 208/139 |
| 4,568,783 A | 2/1986 | Pedersen et al. | |
| 6,380,450 B1 | 4/2002 | Matsumura | |

FOREIGN PATENT DOCUMENTS

| | | |
|---|---|---|
| JP | S50-033993 | 4/1975 |
| JP | S54-039060 | 3/1979 |
| JP | 2000-063298 | 2/2000 |
| JP | 2000-063299 | 2/2000 |
| JP | 2013-133293 | 7/2013 |
| JP | 2017-165667 | 9/2017 |
| JP | 2017-210461 | 11/2017 |

OTHER PUBLICATIONS

Takahashi, Katsumi et al., "Liquid tellurium as a catalyst for the dehydrogenation of several polynuclear hydrocarbons", Chemistry Letters, 1978, No. 4, ISSN 0366-7002, pp. 423-425.
Miyata, Kaoru et al., "Activity of a tellurium-magnesia catalyst prepared by adsorption of tellurium vapor onto magnesia: dehydrogenation activity for aromatic hydrocarbons", Sekiyu Gakkaishi, vol. 31, No. 3, 1988, ISSN 0582-4664, pp. 210-215.
ISR issued in WIPO Patent Application No. PCT/JP2019/016050, Jul. 9, 2019, English translation.
IPRP issued in WIPO Patent Application No. PCT/JP2019/016050, Nov. 5, 2020, English translation.
Hiroshi Yasui, "Concerning Platinum Catalysts for Modification", Mar. 31, 1985, vol. 11, pp. 1-9, partial translation.

* cited by examiner

*Primary Examiner* — Youngsul Jeong
*Assistant Examiner* — Jason Y Chong
(74) *Attorney, Agent, or Firm* — Greenblum & Bernstein, P.L.C.

(57) ABSTRACT

The present invention provides a production method for indene, comprising a dehydrogenation step of obtaining a reaction product containing indene by contacting a raw material gas containing indane and molecular hydrogen with a dehydrogenation catalyst, wherein the dehydrogenation catalyst comprises a support containing aluminum, and a supported metal supported on the support, the supported metal contains a group 14 metal element and platinum, and an atomic ratio of the group 14 metal element to the platinum in the dehydrogenation catalyst is 8.0 or less.

6 Claims, No Drawings

METHOD FOR PRODUCING INDENE

TECHNICAL FIELD

The present invention relates to a production method for indene.

BACKGROUND ART

Indene is an industrially useful substance as a material of a coumarone-indene resin or an optical resin. As a production method for indene, a method for collecting indene from a coal tar fraction is known, but since a coal tar fraction contains a large number of impurities such as benzonitrile and benzofuran, when a separation/collection method through distillation is employed, it is difficult to obtain indene with high impurity particularly with benzonitrile having a close boiling point separated. As a method for producing indene with high impurity, a method of directly performing dehydrogenation reaction of tetrahydroindene is known (Patent Literatures 1 to 3).

CITATION LIST

Patent Literature

Patent Literature 1: Japanese Unexamined Patent Publication No. 2000-63298
Patent Literature 2: Japanese Unexamined Patent Publication No. 2000-63299
Patent Literature 3: Japanese Unexamined Patent Publication No. 2013-133293

SUMMARY OF INVENTION

Technical Problem

An object of the present invention is to provide, as a novel production method for indene, a method for dehydrogenating indane in which indene can be efficiently produced from indane.

Solution to Problem

The present inventors have found that indene can be efficiently produced from indane by performing dehydrogenation reaction using a specific dehydrogenation catalyst in the coexistence of molecular hydrogen, resulting in accomplishing the present invention. It is known that when molecular hydrogen is coexistent in dehydrogenation reaction, the yield is lowered from the viewpoint of thermodynamic equilibrium constraint in general. The present inventors have found, however, that when a specific dehydrogenation catalyst is used, reaction efficiency in dehydrogenation reaction of indane is improved and indene can be efficiently obtained by deliberately allowing molecular hydrogen to coexist.

One aspect of the present invention relates to a production method for indene comprising a dehydrogenation step of obtaining a reaction product containing indene by contacting a raw material gas containing indene and molecular hydrogen with a dehydrogenation catalyst. In this production method, the dehydrogenation catalyst comprises a support containing aluminum, and a supported metal supported on the support, the supported metal includes a group 14 metal element and platinum, and an atomic ratio of the group 14 metal element to the platinum in the dehydrogenation catalyst is 8.0 or less.

In one aspect, the atomic ratio of the group 14 metal element to the platinum in the dehydrogenation catalyst may be 3.5 or more and 7.0 or less.

In one aspect, the group 14 metal element may be tin.

In one aspect, the group 14 metal element and the platinum may be supported on the support by using a metal source not containing a chlorine atom.

In one aspect, a molar ratio of the molecular hydrogen to the indene in the raw material gas may be 3.5 or less.

In one aspect, the production method may further comprise a raw material synthesis step of obtaining indane by dehydrogenation reaction of tetrahydroindene.

Advantageous Effects of Invention

According to the present invention, a dehydrogenation method for indene in which indene can be efficiently produced from indane is provided as a novel production method for indene.

DESCRIPTION OF EMBODIMENTS

Now, a preferable embodiment of the present invention will be described, and it is noted that the present invention is not limited to the following embodiment.

A production method for indene of the present embodiment comprises a dehydrogenation step of obtaining a reaction product containing indene by contacting a raw material gas containing indene and molecular hydrogen (hereinafter sometimes simply referred to as hydrogen) with a dehydrogenation catalyst.

In the present embodiment, the dehydrogenation catalyst comprises a support containing aluminum (Al), and a supported metal supported on the support. Besides, the supported metal includes a group 14 metal element and platinum (Pt). An atomic ratio of the group 14 metal element to the platinum in the dehydrogenation catalyst is 8.0 or less.

According to the production method of the present embodiment, indene can be efficiently produced from indene. It is known that when molecular hydrogen is coexistent in dehydrogenation reaction, the yield is lowered from the viewpoint of thermodynamic equilibrium constraint in general. The present inventors have found, however, that when a specific dehydrogenation catalyst is used, reaction efficiency in dehydrogenation reaction of indane is improved by deliberately allowing molecular hydrogen to coexist. Specifically, according to the production method of the present embodiment, indene can be efficiently produced by using a specific dehydrogenation catalyst and allowing hydrogen to coexist.

The dehydrogenation catalyst of the present embodiment will now be described in detail.

The dehydrogenation catalyst used in the present embodiment is a catalyst comprising a support containing aluminum, and a supported metal supported on the support. The supported metal includes a group 14 metal element and platinum. Here, a group 14 metal element means a metal element belonging to the group 14 of the long-form periodic table of elements based on the definition of IUPAC (International Union of Pure and Applied Chemistry). Examples of the group 14 metal element include tin (Sn) and lead (Pb).

A method for preparing the dehydrogenation catalyst is not especially limited, and may be a method in which the group 14 metal element is caused to be supported on the support, and then platinum is further caused to be supported thereon, a method in which platinum is caused to be supported on the support, and then the group 14 metal element is further caused to be supported thereon, or a method in which the group 14 metal element and platinum are simultaneously caused to be supported on the support.

The support is preferably an inorganic oxide support containing aluminum. The support may be, for example, a support containing alumina ($Al_2O_3$), or a support containing a complex oxide of Al and another metal. More specifically, a metal oxide support may be, for example, a support containing a metal oxide such as alumina, a complex oxide of Al and Mg, a complex oxide of Al and Sn, a complex oxide of Al and Pb, or a complex oxide of Al and Zn, Se, Fe, In or the like. A content of Al in the support may be 25% by mass or more, and is preferably 50% by mass or more based on the whole mass of the support. An example of the inorganic oxide support containing Al includes a support containing an inorganic oxide such as alumina, alumina magnesia, silica alumina, zirconia alumina, or a spinel structure (magnesium spinel).

A method for preparing the support is not especially limited, and examples include a sol-gel method, a coprecipitation method, and a hydrothermal method.

A specific surface area of the support may be, for example, 30 $m^2$/g or more, and is preferably 50 $m^2$/g or more. Thus, the conversion rate of indane tends to be further improved. The specific surface area of the support may be, for example, 1000 $m^2$/g or less, and is preferably 500 $m^2$/g or less. When the support has such a specific surface area, the support attains sufficient strength to be suitably industrially applicable. It is noted that the specific surface area of the support is measured with a BET specific surface area meter employing a nitrogen adsorption method.

In the dehydrogenation catalyst, the supported metal including the group 14 metal element and platinum may be present in the form of a single oxide, may be present in the form of a complex oxide with another metal, or may be present in the form of a metal salt or a metal simple substance.

The dehydrogenation catalyst may be one obtained by causing the supported metal to be supported on the support by using a metal source (a compound containing the supported metal).

Examples of a platinum source include tetraammineplatinous(II) acid, tetraammineplatinum(II) acid salt (such as nitrate), a tetraammineplatinous(II) hydroxide solution, a dinitrodiammineplatinous(II) nitric acid solution, a hexahydroxoplatinic(IV) nitric acid solution, and a hexahydroxoplatinic(IV) ethanolamine solution. The platinum source is preferably a compound containing platinum (platinum) but not containing a chlorine atom.

An amount of platinum supported is 0.1% by mass or more, and preferably 0.5% by mass or more based on the whole amount of the dehydrogenation catalyst. The amount of platinum supported is 5.0% by mass or less, and preferably 3.0% by mass or less based on the whole amount of the dehydrogenation catalyst. When such an amount supported is employed, a platinum particle to be formed on the catalyst can be made to have a size suitable for the dehydrogenation reaction, and a platinum surface area per unit platinum weight is increased, and therefore, a more efficient reaction system can be realized.

An example of the group 14 metal element is tin. Examples of a tin source include sodium stannate, and potassium stannate. The tin source is preferably a compound containing tin (Sn) but not containing a chlorine atom.

In the dehydrogenation catalyst, an atomic ratio (M/Pt) of the group 14 metal element (M) to the platinum (Pt) is 8.0 or less, preferably 6.5 or less, and more preferably 5.0 or less. The atomic ratio (M/Pt) of the group 14 metal element (M) to the platinum (Pt) is preferably 1.0 or more, and more preferably 3.5 or more. When the atomic ratio falls in the above-described range, the yield of indene tends to be further improved.

The dehydrogenation catalyst may further comprise another metal element in addition to the group 14 metal element and the platinum. Examples of another metal element include lithium (Li), sodium (Na), potassium (K), magnesium (Mg), calcium (Ca), zin (Zn), iron (Fe), indium (In), selenium (Se), antimony (Sb), nickel (Ni), and gallium (Ga).

A supporting method for the supported metal is not especially limited, and examples include an impregnation method, a deposition method, a coprecipitation method, a kneading method, an ion exchange method, and a pore filling method.

One aspect of the supporting method will now be described. First, a support is added to a solution containing a precursor (metal source) of a supported metal, and the resultant support containing the solution is kneaded. Thereafter, a solvent is removed by drying, the thus obtained solid is baked, and thus, the supported metal can be supported on the support.

The precursor of the supported metal is preferably a metal source not containing a chlorine atom. When a metal source not containing a chlorine atom is used as the precursor, corrosion of an apparatus used in the preparation of the catalyst can be prevented.

Baking can be performed, for example, in an air atmosphere or in an oxygen atmosphere. The baking may be performed in single stage, or in multiple stages of two or more stages. A baking temperature may be a temperature at which the precursor of the supported metal can be decomposed, and for example, may be 200 to 1000° C., or may be 400 to 800° C. Incidentally, when the baking is performed in multiple stages, the baking temperature may be employed in at least one of the stages. Baking temperatures employed in the other stages may be, for example, in the same range as described above, or may be 100 to 200° C.

From the viewpoint of improvement of moldability, the dehydrogenation catalyst may further comprise a molding aid. The molding aid may be, for example, a thickener, a surfactant, a water retention agent, a plasticizer, or a hinder material.

A shape of the dehydrogenation catalyst is not especially limited, and may be, for example, a pellet shape, a granular shape, a honeycomb shape, or a sponge shape. Besides, the dehydrogenation catalyst may be molded by a method such as an extruding method or a tableting method.

Next, the dehydrogenation step of the present embodiment will be described in detail.

The dehydrogenation step is a step of obtaining a reaction product containing indene by contacting a raw material gas containing indane and molecular hydrogen (hereinafter sometimes simply referred to as hydrogen) with the dehydrogenation catalyst. In the dehydrogenation step, at least a part of indane is converted into indene through the dehydrogenation reaction. In the present embodiment, since the raw material gas contains hydrogen, the dehydrogenation reaction proceeds in the presence of hydrogen.

In the raw material gas, a molar ratio (molecular hydrogen/indane) of the molecular hydrogen to the indane is preferably 5.0 or less, and more preferably 3.5 or less. Thus, the influence of the thermodynamic equilibrium constraint is reduced, and hence the dehydrogenation reaction tends to more efficiently proceed. The molar ratio (molecular hydrogen/indene) of the molecular hydrogen to the indene in the raw material gas is preferably 0.01 or more, and more preferably 0.05 or more. Thus, the effect attained by the presence of the molecular hydrogen can be more remarkably attained, and hence indene can be obtained in high yield.

The raw material gas may further contain an inert gas such as nitrogen or argon in addition to the indene and the molecular hydrogen. Besides, the raw material gas may further contain steam. The raw material gas may further contain carbon monoxide, a carbon dioxide gas, an alkane, an olefin, or the like. A total content of components contained in addition to the indane and the molecular hydrogen may be, for example, 10.0-fold moles or less with respect to indane, is preferably 5.0-fold moles or less with respect to indane, or may be 0 (zero).

In the dehydrogenation step, the dehydrogenation reaction may be performed, for example, by using a reactor filled with the dehydrogenation catalyst, and by causing the raw material gas to pass through the reactor. As the reactor, any of various reactors used for a gas phase reaction using a solid catalyst can be used. Examples of the reactor include a fixed bed adiabatic reactor, a radial flow reactor, and a tubular reactor.

A reaction method for the dehydrogenation reaction may be, for example, a fixed bed method, a moving bed method, or a fluidized bed method. Among these, the fixed bed method is preferred from the viewpoint of equipment cost.

A temperature at which the raw material gas is contacted with the dehydrogenation catalyst (which can be said as a reaction temperature of the dehydrogenation reaction, or a temperature within the reactor) may be, from the viewpoint of reaction efficiency, for example, 350 to 800° C., may be 400 to 700° C., and may be 450° C. to 650° C. When the reaction temperature is 350° C. or more, the yield of indene tends to be further improved because equilibrium conversion of indene is not too low. When the reaction temperature is 800° C. or less, the dehydrogenation catalyst can retain its high activity for a longer period of time because a coke generation rate is restrained.

A pressure at which the raw material gas is contacted with the dehydrogenation catalyst (which can be said as a reaction pressure of the dehydrogenation reaction, or a pressure within the reactor) may be, for example, 0.01 to 4.0 MPa, may be 0.03 to 0.5 MPa, or may be 0.01 to 0.3 MPa. When the reaction pressure falls in the above-described range, the dehydrogenation reaction tends to easily proceed to obtain further excellent reaction efficiency.

When the dehydrogenation step is performed by a continuous reaction method for continuously supplying a raw material, a weight hourly space velocity (hereinafter referred to as the "WHSV") may be 0.01 $h^{-1}$ or more, or may be 0.1 $h^{-1}$ or more. When such a WHSV is employed, the conversion rate of indane can be further increased. The WHSV may be 100 $h^{-1}$ or less, or may be 20 $h^{-1}$ or less. When such a WHSV is employed, the reactor size can be further reduced. Here, the WHSV refers to a ratio (F/W) of a supply rate (amount supplied/time) F of the raw material to the mass W of the dehydrogenation catalyst in a continuous reaction device. It is noted that further preferable ranges of amounts of the raw material and the catalyst used may be appropriately selected in accordance with reaction conditions, the activity of the catalyst and the like, and the WHSV is not limited to the above-described range.

The production method of the present embodiment may further include the raw material synthesis step of obtaining indane by dehydrogenation reaction of tetrahydroindene.

In such a production method, a downstream side of the reactor may be filled with the dehydrogenation catalyst (hereinafter sometimes referred to as the second dehydrogenation catalyst), and an upstream side of the reactor may be filled with a dehydrogenation catalyst (hereinafter sometimes referred to as the first dehydrogenation catalyst) for converting tetrahydroindene into indane. Since the dehydrogenation catalyst (the second dehydrogenation catalyst) is excellent in the reaction activity of the dehydrogenation reaction from indane to indene, when the upstream stage of the second dehydrogenation catalyst is filled with the first dehydrogenation catalyst, indene can be efficiently produced from tetrahydroindene.

As the first dehydrogenation catalyst, any one of solid catalysts for catalyzing dehydrogenation reaction of tetrahydroindene can be used without any limitation. As the first dehydrogenation catalyst, for example, a chromium/$Al_2O_3$ catalyst, a platinum/$Al_2O_3$, catalyst and a Fe—K catalyst, which are used as catalysts for dehydrogenation reaction, or a Bi—Mo catalyst usually used as a catalyst for oxidative dehydrogenation reaction can be used.

As described so far, according to the production method of the present embodiment, high indene yield can be obtained by using a specific dehydrogenation catalyst in the coexistence of molecular hydrogen. Therefore, according to the production method of the present embodiment, indene can be efficiently produced from indane. Therefore, the production method of the present embodiment is very useful for industrially producing indene.

EXAMPLES

Now, the present invention will be more specifically described with reference to examples, and it is noted that the present invention is not limited to these examples.

Catalyst Synthesis Example 1

<Preparation of Dehydrogenation Catalyst A> 20.0 g of commercially available γ-alumina (manufactured by JGC Catalysts and Chemicals Ltd.) was mixed with an aqueous solution obtained by dissolving 25.1 g of magnesium nitrate hexahydrate (manufactured by Wako Pure Chemical Industries Ltd., $Mg(NO_3)_2 \cdot 6H_2O$) in water (about 150 ml), followed by removing water therefrom with an evaporator at about 50° C. Thereafter, the resultant was dried at 130° C. overnight, and then baked at 550° C. for 3 hours, and subsequently at 800° C. for 3 hours. The thus obtained baked product was mixed with an aqueous solution obtained by dissolving 25.1 g of magnesium nitrate hexahydrate (manufactured by Wako Pure Chemical Industries Ltd., $Mg(NO_3)_2 \cdot 6H_2O$) in water (about 150 ml), followed by removing water therefrom with an evaporator at about 50° C. Thereafter, the resultant was dried at 130° C. overnight, and then baked at 550° C. for 3 hours, and subsequently at 800° C. for 3 hours. In this manner, an alumina-magnesia support having a spinel structure was obtained. It is noted that the alumina-magnesia support thus obtained was found to have a diffraction peak derived from Mg spine at 2θ of 36.9, 44.8, 59.4, and 65.3 degrees through X-ray diffraction measurement.

5.0 g of the alumina-magnesia support was mixed with an aqueous solution obtained by dissolving 0.37 g of sodium stannate (manufactured by KISHIDA CHEMICAL Co., Ltd., $Na_2SnO_3 \cdot 3H_2O$) in 10 ml of water in advance, so as to impregnation support tin in such a manner that a final amount of tin supported after a dehydrogenation catalyst was prepared was 2.7% by mass. Thereafter, the resultant was dried at 130° C. overnight, and then baked at 550° C. for 3 hours, followed by repeatedly washing with water. Subsequently, a dinitrodiammineplatinous(II) nitric acid solution (manufactured by TANAKA Kikinzoku Kogyo K.K., $[Pt(NH_3)_2(NO_2)_2]/HNO_3$) was used to impregnation support platinum in such a manner that an amount of platinum supported was 1.0% by mass, and the resultant was dried at 130° C. overnight, and then baked at 550° C. for 3 hours to obtain a dehydrogenation catalyst A.

[Catalyst Synthesis Example 2]
<Preparation of Dehydrogenation Catalyst B>

A dehydrogenation catalyst B was prepared in the same manner as in Catalyst Synthesis Example 1 except that tin and platinum were supported in such a manner that an amount of tin supported was 8.3% by mass and an amount of platinum supported was 3.0% by mass.

[Catalyst Synthesis Example 3]
<Preparation of Dehydrogenation Catalyst C>

A dehydrogenation catalyst C was prepared in the same manner as in Catalyst Synthesis Example 1 except that tin was supported in such a manner that an amount of tin supported was 1.8% by mass.

[Catalyst Synthesis Example 4]
<Preparation of Dehydrogenation Catalyst D>

A dehydrogenation catalyst D was prepared in the same manner as in Catalyst Synthesis Example 1 except that tin was supported in such a manner that an amount of tin supported was 5.5% by mass.

Example 1

A tubular reactor was filled with 2.0 g of the dehydrogenation catalyst A, and a reaction tube was connected to a fixed bed flow reaction device. The reaction tube was heated to 515° C., and this state was retained for 0.5 hours with molecular hydrogen allowed to pass therethrough at 99 mL/min. Thereafter, indane (manufactured by Tokyo Chemical Industry Co., Ltd.) and hydrogen were respectively supplied to the reactor, and dehydrogenation reaction of indane was performed at a reaction temperature of 515° C. and 0.1 MPa. A composition supplied to the reactor was set to indane:hydrogen ($H_2$)=1.0:0.2 (molar ratio). The WHSV was set to 3.0 $h^{-1}$.

After elapse of 300 minutes from the start of the reaction, a product of the dehydrogenation reaction was collected from the tubular reactor. It is noted that the start of the reaction refers to a time when the supply of the raw material was started. The thus collected product was analyzed by using a gas chromatograph equipped with a flame ionization detector (HD-GC). Based on a result obtained by the gas chromatograph, components (unit: % by mass) of the collected product were quantitatively determined. Results are shown in Table 1.

The conversion rate of indane, the selectivity of indene, and the yield of indene are respectively defined by the following expressions (1), (2) and (3):

$$r_C = \{1-(m_1/m_0)\} \times 100 \quad (1)$$

$$r_S = \{m_2/(m_0-m_1)\} \times 100 \quad (2)$$

$$r_Y = (m_2/m_0) \times 100 \quad (3)$$

$r_C$ of the expression (1) represents the conversion rate (%) of indane. $m_0$ represents the molar number of indane present in a raw material. $m_1$ represents the molar number of indane remaining in a product. $r_S$ of the expression (2) represents the selectivity (%) of indene. $m_2$ represents the molar number of indene contained in the product. $r_Y$ of the expression (3) represents the yield (%) of indene.

Example 2

Dehydrogenation reaction was performed in the same manner as Example 1 except that the tubular reactor was filled with 2.0 g of the dehydrogenation catalyst B instead of the dehydrogenation catalyst A, and that the raw material composition was set to indane:hydrogen ($H_2$)=1.0:2.5 (molar ratio). Results are shown in Table 1.

Example 3

Dehydrogenation reaction was performed in the same manner as Example 1 except that the tubular reactor was filled with 2.0 g of the dehydrogenation catalyst B instead of the dehydrogenation catalyst A, and that the raw material composition was set to indane:hydrogen ($H_2$)=1.0:0.6 (molar ratio). Results are shown in Table 1.

Example 4

Dehydrogenation reaction was performed in the same manner as Example 1 except that the tubular reactor was filled with 2.0 g of the dehydrogenation catalyst B instead of the dehydrogenation catalyst A. Results are shown in Table 1.

Example 5

Dehydrogenation reaction was performed in the same manner as Example 1 except that the tubular reactor was filled with 2.0 g of the dehydrogenation catalyst C instead of the dehydrogenation catalyst A. Results are shown in Table 1.

Comparative Example 1

A tubular reactor was filled with 2.0 g of the dehydrogenation catalyst B, and a reaction tube was connected to a fixed bed flow reaction device. The reaction tube was heated to 515° C., and this state was retained for 0.5 hours with molecular hydrogen allowed to pass therethrough at 99 mL/min. Subsequently, with the reaction tube kept at 515° C., a mixed gas of $N_2$ and steam (water) ($N_2$:steam=1.0:2.1 (molar ratio)) was allowed to pass therethrough at 15.4 mL/min for 30 minutes. Thereafter, indane (manufactured by Tokyo Chemical Industry Co., Ltd.), $N_2$ and steam (water) were respectively supplied to the reactor, and dehydrogenation reaction of indane was performed at a reaction temperature of 515° C. and 0.1 MPa. The composition supplied to the reactor was set to indane:$N_2$:steam (water)=1.0:0.3:2.3 (molar ratio). The WHSV was set to 3.0 $h^{-1}$.

After elapse of 300 minutes from the start of the reaction, a product of the dehydrogenation reaction was collected from the tubular reactor. It is noted that the start of the reaction refers to a time when the supply of the raw material was started. The thus collected product was analyzed by using a gas chromatograph equipped with a flame ionization detector (FID-GC). Based on a result obtained by the gas chromatograph, components (unit: % by mass) of the collected product were quantitatively determined. Results are shown in Table 2.

Comparative Example 2

Dehydrogenation reaction was performed in the same manner as Comparative Example 1 except that the dehydrogenation catalyst C was used instead of the dehydrogenation catalyst B. Results are shown in Table 2.

Comparative Example 3

Dehydrogenation reaction was performed in the same manner as Comparative Example 1 except that the dehydrogenation catalyst D was used instead of the dehydrogenation catalyst B. Results are shown in Table 2.

Comparative Example 4

Dehydrogenation reaction was performed in the same manner as Example 1 except that the dehydrogenation catalyst D was used instead of the dehydrogenation catalyst A. Results are shown in Table 2.

INDUSTRIAL APPLICABILITY

According to the present invention, industrially useful indene can be efficiently produced from indane.

The invention claimed is:

1. A production method for indene, comprising obtaining a reaction product containing indene by contacting a raw material gas containing indane and molecular hydrogen with a dehydrogenation catalyst,
   wherein the dehydrogenation catalyst comprises a support containing aluminum, and a metal supported on the support,
   the metal contains a group 14 metal element and platinum, and
   an atomic ratio of the group 14 metal element to the platinum in the dehydrogenation catalyst is 8.0 or less.

2. The production method according to claim 1, wherein the atomic ratio of the group 14 metal element to the platinum in the dehydrogenation catalyst is 3.5 or more and 7.0 or less.

3. The production method according to claim 1, wherein the group 14 metal element is tin.

4. The production method according to claim 1, wherein the group 14 metal element and the platinum are supported on the support by using a metal source not containing a chlorine atom.

5. The production method according to claim 1, wherein a molar ratio of the molecular hydrogen to the indane in the raw material gas is 3.5 or less.

TABLE 1

|  |  | Example 1 | Example 2 | Example 3 | Example 4 | Example 5 |
|---|---|---|---|---|---|---|
| Dehydrogenation Catalyst |  | A | B | B | B | C |
| Pt | mass % | 1 | 3 | 3 | 3 | 1 |
| Sn | mass % | 2.7 | 8.3 | 8.3 | 8.3 | 1.8 |
| Sn/Pt | Atomic Ratio | 4.5 | 4.5 | 4.5 | 4.5 | 3.0 |
| $H_2$/Indane | Molar Ratio | 0.2 | 2.5 | 0.6 | 0.2 | 0.2 |
| $H_2$/Indane | Molar Ratio | — | — | — | — | — |
| $H_2O$/Indane | Molar Ratio | — | — | — | — | — |
| Conversion Rate of Indane | % | 31 | 27 | 28 | 26 | 24 |
| Selectivity of Indene | % | 80 | 84 | 84 | 84 | 85 |
| Yield of Indene | % | 25 | 23 | 23 | 22 | 20 |

TABLE 2

|  |  | Comparative Example 1 | Comparative Example 2 | Comparative Example 3 | Comparative Example 4 |
|---|---|---|---|---|---|
| Dehydrogenation Catalyst |  | B | C | D | D |
| Pt | mass % | 3 | 1 | 1 | 1 |
| Sn | mass % | 8.3 | 1.8 | 5.5 | 5.5 |
| Sn/Pt | Atomic Ratio | 4.5 | 3.0 | 9.0 | 9.0 |
| $H_2$/Indane | Molar Ratio | — | — | — | 0.2 |
| $N_2$/Indane | Molar Ratio | 0.3 | 0.3 | 0.3 | — |
| $H_2O$/Indane | Molar Ratio | 2.3 | 2.3 | 2.3 | — |
| Conversion Rate of Indane | % | 17 | 22 | 23 | 24 |
| Selectivity of Indene | % | 80 | 74 | 81 | 80 |
| Yield of Indene | % | 14 | 16 | 19 | 19 |

6. The production method according to claim 1, further comprising obtaining the indane by dehydrogenation reaction of tetrahydroindene.

\* \* \* \* \*